(12) United States Patent
Kawashima et al.

(10) Patent No.: US 6,550,110 B1
(45) Date of Patent: Apr. 22, 2003

(54) STRAP CLAMPING BLOCKS FOR SWIMMING GOGGLES

(75) Inventors: Haruo Kawashima, Tokyo (JP); Shunji Fukasawa, Tokyo (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/496,774

(22) Filed: Feb. 3, 2000

(30) Foreign Application Priority Data

Feb. 4, 1999 (JP) .......................................... 11-027889

(51) Int. Cl.[7] .............................................. A44B 11/04
(52) U.S. Cl. ...................................... 24/265 BC; 24/3.3
(58) Field of Search ........................ 24/265 BC, 265 A, 24/265 AL, 265 EC, 3.3; 2/428–430, 452; 351/43, 156

(56) References Cited

U.S. PATENT DOCUMENTS

| | | | | |
|---|---|---|---|---|
| 3,397,026 A | * | 8/1968 | Spina | 351/157 |
| 4,313,243 A | * | 2/1982 | Childress et al. | 24/136 K |
| 4,783,164 A | * | 11/1988 | Heiberger | 351/156 |
| 4,881,803 A | * | 11/1989 | Giles et al. | 351/156 |
| 4,912,814 A | * | 4/1990 | McKenzie | 24/115 H |
| 5,454,140 A | * | 10/1995 | Murai | 24/115 H X |
| 5,541,676 A | * | 7/1996 | Pallat | 351/156 |
| 5,706,526 A | | 1/1998 | Huang | 2/428 |
| 5,894,639 A | * | 4/1999 | Boden et al. | 24/115 G |
| 5,915,540 A | * | 6/1999 | Chou | 2/428 |
| 6,029,870 A | * | 2/2000 | Giancona, III | 224/148.6 |

* cited by examiner

*Primary Examiner*—William Miller
*Assistant Examiner*—Ruth C. Rodriguez
(74) *Attorney, Agent, or Firm*—Butzel Long

(57) ABSTRACT

A strap clamping block for swimming goggles, having a pair of guiding channels which are independent of each other and adapted to guide two sections of a strap extending in parallel to each other, respectively. The guiding channels respectively have separator surfaces curved, in the vicinity of a rear end of the clamping block, so as to separate the two sections of the strap up- and downward from each other.

4 Claims, 2 Drawing Sheets

STRAP CLAMPING BLOCKS FOR SWIMMING GOGGLES

BACKGROUND OF THE INVENTION

This invention relates to strap clamping blocks for swimming goggles and more particularly to such strap clamping blocks adapted to converge upper and lower sections of a strap at appropriate locations thereof so that these sections extend in parallel to each other.

U.S. Pat. No. 5,706,526 issued to Ann Huang on Jan. 13, 1998 discloses a pair of swimming goggles including a pair of strap clamping blocks adapted to converge upper and lower strap sections extending in parallel to each other from the associated outer end of a main frame body in the vicinity of said outer end so that said clamping blocks may prevent the straps of the goggles put on a wearer's head from applying pressure toward the wearer's ears.

Each of the known clamping blocks includes a bore extending longitudinally therethough and the upper and lower strap sections are guided together through the bore. Such an arrangement may often cause a problem. For example, when one tries to adjust a length of the strap so that the goggles may be properly put around the wearer's head by pulling one of the two sections longitudinally thereof, the one section may interfere with the other section of the strap and thereby obstruct the ability to make the desired adjustment. Usually, the upper and lower strap sections of the strap or straps are guided through a pair of strap clamping blocks provided adjacent the goggles extend rearward from the respective clamping blocks to the middle region between the pair of clamping blocks so that the upper and lower strap sections may be progressively separated up- and downward from each other. Such arrangement aims to ensure that the swimming goggles can be stabilized on the wearer's head. On the contrary, the known clamping block functions merely to converge the upper and lower strap sections in contact with each other. As a result, in the vicinity of the block, the two strap sections are forcibly bent against their elasticity so that they are spaced from each other, i.e., up- and downward, respectively. Necessarily, the upper and lower strap sections are biased to restore their initial positions and, during use of the swimming goggles, a space between the upper and lower strap sections may be excessively reduced to stabilize the swimming goggles on the wearer's head.

SUMMARY OF THE INVENTION

It is an object of this invention to improve the strap clamping blocks for the swimming goggles, each of the strap clamping blocks having longitudinally opposite ends, transversely opposite side edges, opposite flanks contoured by the ends and side edges, and a strap guiding bore extending therethrough longitudinally of the strap.

According to this invention, there is provided a strap clamping block for swimming goggles having longitudinally opposite ends, transversely opposite side edges, opposite flanks each contoured by the ends and side edges, and a pair of strap guiding channels extending therethrough in a longitudinal direction of a strap used by the swimming goggles, wherein: the pair of guiding channels extending in the longitudinal direction between the opposite side edges so as to present a first separator surface facing one of the opposite side edges and a second separator surface facing the other side edge, respectively, wherein the first and second separator surfaces are respectively defined by slopes curved to go away from each other progressively toward a rear end of the clamping block.

According to one embodiment of this invention, a space between the opposite side edges in the vicinity of the rear end of the clamping block is reduced progressively toward the rear end.

According to another embodiment of this invention, a thickness of the clamping block as measured between the opposite flanks is smaller than a width of the clamping block as measured between the opposite side edges.

According to still another embodiment of this invention, each of the strap guiding channels is dimensioned, in a cross-section thereof taken in a transverse direction of the clamping block, to have a length as measured in the transverse direction larger than a length as measured between the opposite flanks.

DESCRIPTION OF THE PREFERRED EMBODIMENTS

Figure 1:
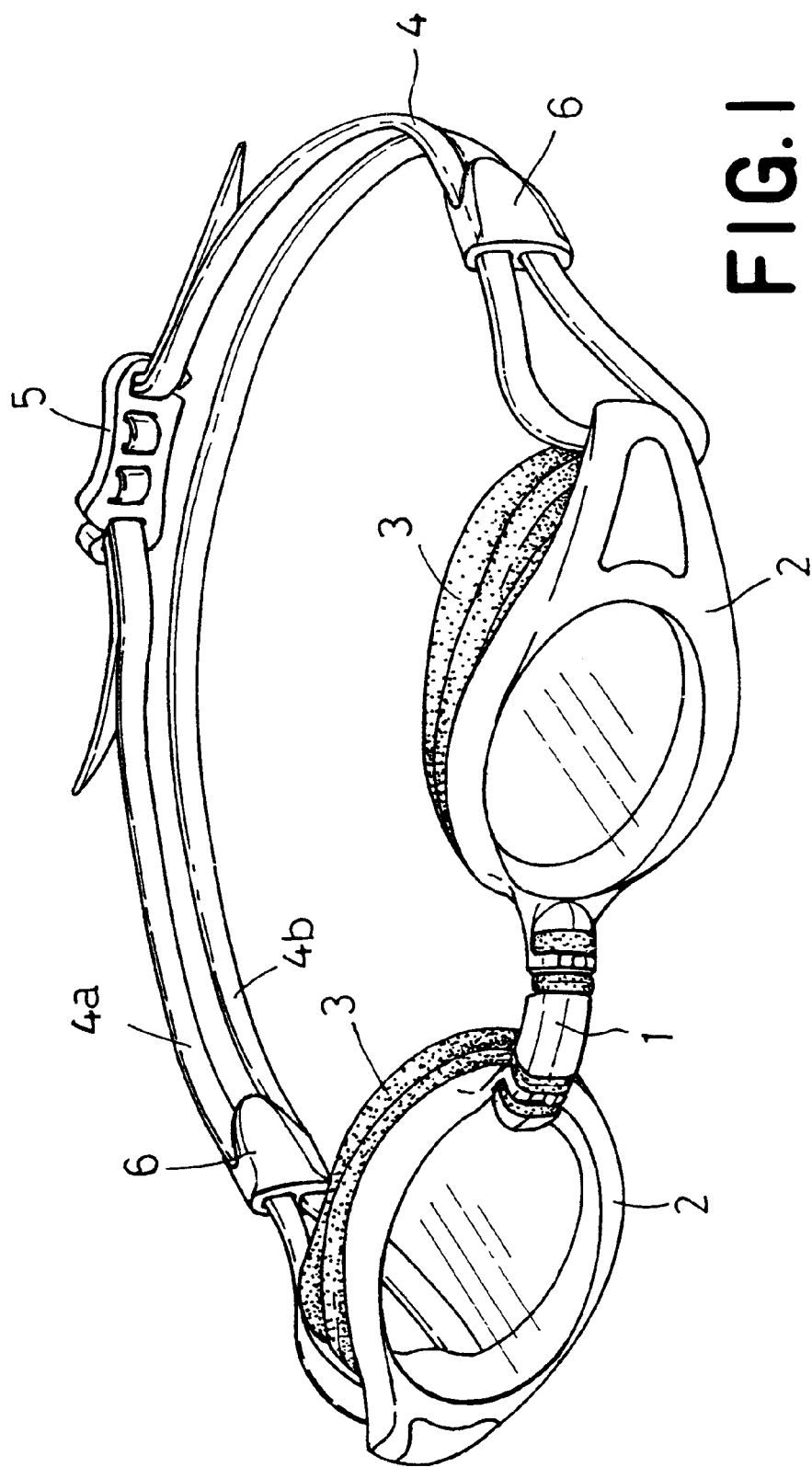
FIG. 1 is a perspective view of a pair of swimming goggles according to this invention.

FIG. 1 is a perspective view of complete swimming goggles. The goggles comprise a pair of lens frames 2 interconnected by a bridge 1, each of the lens frames 2 comprising a lens and a frame integrally molded from hard plastic, a pair of pads 3 molded from soft plastic, rubber or the like and fixed to rear surfaces of the respective lens frames 2, a strap 4 molded from soft plastic, rubber or the like and looped through the outer ends of the respective lens frames 2, a buckle 5 and a pair of strap clamping blocks 6 both of which are put around the strap 4.

The strap 4 is provided in the form of a single strap looped through the outer ends of the respective lens frames 2 so that a pair of strap sections 4a, 4b may extend rearward from the outer ends substantially in parallel to each other. Longitudinally opposite ends of the strap 4 are coupled together by the buckle 5. Each of the clamping blocks 6 is put on the pair of strap sections 4a, 4b in the vicinity of the associated lens frame 2.

Figure 2:
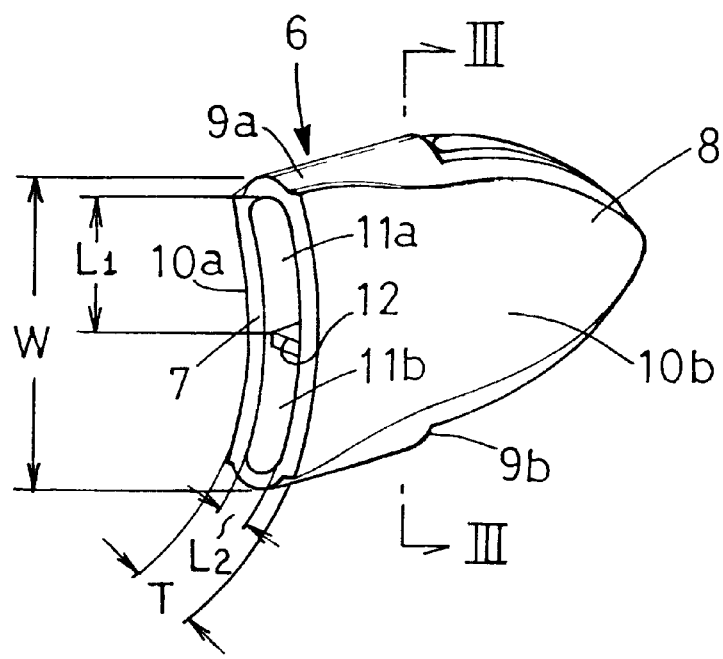
FIG. 2 is a perspective view of a strap clamping block according to this invention.
Figure 3:
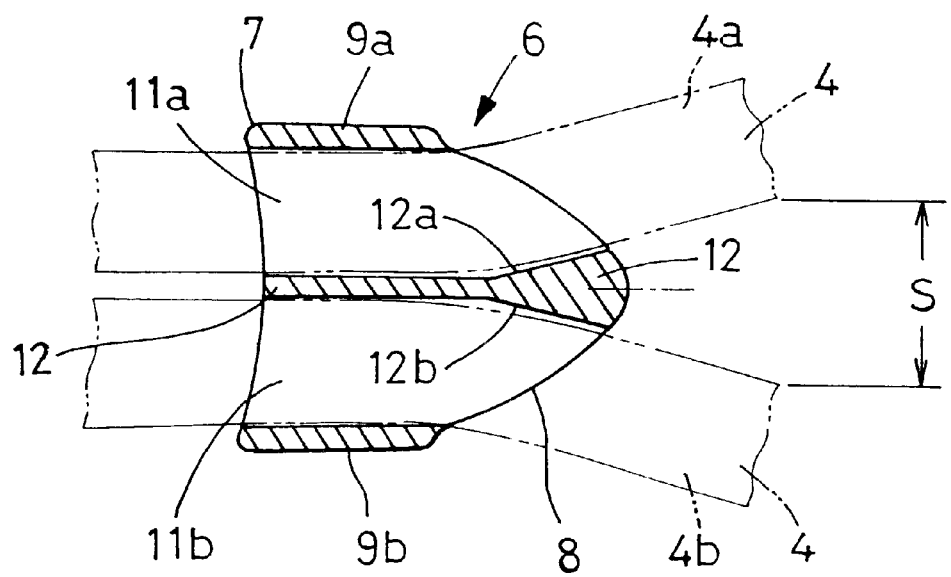
FIG. 3 is a sectional view taken in a direction as indicated by a line III—III in FIG. 2.

FIG. 2 is a perspective view of the clamping block 6 and FIG. 3 is a sectional view taken in a direction as indicated by a line III—III in FIG. 2. The clamping block 6 is molded from hard plastic and has longitudinally opposite ends 7, 8, transversely opposite side edges 9a, 9b, opposite flanks 10a, 10b contoured by said ends 7, 8 and the side edges 9a, 9b, a pair of strap guiding channels 11a, 11b extending therethrough longitudinally of the strap 4. The pair of strap guiding channels 11a, 11b are separated by a partition 12 extending between the opposite flanks 10a, 10b longitudinally of the strap 4. The partition 12 has a separator surface 12a facing the side edge 9a and a separator surface 12b facing the side edge 9b. The separator surfaces 12a, 12b are defined by slopes which are surved to be spaced from each other progressively toward the rear end of the clamping block 6 (to the right hand as viewed in FIG. 3). Substantially in a rear half of the clamping block 6, the opposite flanks 10a, 10b have a width progressively reduced toward the rear end of the clamping block 6 and the front end 7 of the clamping block 6 is curved concavely rearwatd. The clamping block 6 presents a substantially flat configuration. Specifically, a thickness T as measured between the opposite flanks 10a, 10b is smaller that a width W as measured between the opposite side edges 9a, 9b. The strap guiding channels 11a, 11b presents their cross-sections which are larger transversely of the clamping block 6. More specifically, a length $L_1$ of said cross-section as measured transversely of the clamping block 6 is larger than a length $L_2$ of the cross-section as measured between the opposite flanks 10a, 10b. The respective strap guiding channels 11a, 11b are dimensioned so that the entire outer surface of the strap 4 may be in slidable contact with inner surfaces of the respective strap guiding channels 11a, 11b.

The pair of strap sections 4a, 4b extending substantially in parallel to each other are slidably guided through the respective strap guiding channels 11a, 11b longitudinally of the strap 4. Usually, the strap clamping blocks are provided in the vicinity, of the respective lens frames 2 (See FIG. 1) and function to converge the strap sections so that, during use of the goggles, the wearer's ears may be free from contact with the strap sections in the vicinity of the respective clamping blocks. So far as this function is concerned, the clamping block 6 according to this invention is similar to the previously described clamping block of prior art. As will be apparent from FIG. 3, the clamping block 6 according to this invention additionally functions to separate the pair of sections 4a, 4b of the strap 4 up- and downward from each other along the separator surfaces (slopes) 12a, 12b gently curved in opposite directions substantially in the rear half region of the partition 12. In this manner, the pair of sections 4a, 4b of the strap 4 are separated within the clamping block 6 so as to describe a V-shape with a space S therebetween progressively enlarging to the buckle (See FIG. 1) lying in the middle of the strap 4. Such a unique arrangement allows the pair of strap sections 4a, 4b to naturally remain separated up- and downward from each other even after the clamping block 6 has separated these two sections 4a, 4b at a relatively large angle in order to stabilize the strap 4 around the wearer's head. This is for the reason that, in the vicinity of the clamping block 6, the two sections 4a, 4b are not sharply bent up- and downward against an elasticity of the strap 4 but gently curved up- and downward. With a consequence, it is not apprehended that a restoring force of the strap 4 might uncontrollably move the two strap sections 4a, 4b in close to each other during use of the goggles.

Another advantage provided by the clamping block according to this invention lies in that the two strap sections 4a, 4b are slidably movable along the respective guiding channels 11a, 11b without interfering with each other when one of these two sections 4a, 4b is slidably pulled longitudinally thereof for length-adjustment of the strap 4. Therefore, the desired length-adjustment of the strap 4 can be smoothly carried out. The guiding channels 11a, 11b are separated by the partition 12 so as to be independent of each other and such arrangement of said guiding channels 11a, 11b allows the clamping block 6 to have a substantially flat configuration. Thus, the strap can be stabilized on the wearer's head without a feeling of incompatibility due to a bulkiness of the clamping blocks which would otherwise be experienced by the wearer.

Furthermore, each of the guiding channels 11a, 11b has its cross-sectional shape and size substantially coinciding with those of the strap 4 so that the strap 4 can be properly arranged in upper and lower sections 4a, 4b and be stabilized around the wearer's head without being distorted. Such effect also contributes to stabilization of the strap around the wearer's head without said feeling of incompatibility due to the strap.

As will be apparent from the foregoing description, the clamping block according to this invention is very advantageous to be practically used with the strap of the swimming goggles particularly in view of the fact that this improved clamping block not only facilitates the effective length of the strap to be adjusted and but also contributes to stabilization of the strap around the wearer's head.

What is claimed is:

1. A strap clamping block for swimming goggles, the strap clamping block comprising:

front and rear ends that are longitudinally opposed;

transversely opposite side edges;

opposite flanks each contoured by said front and rear ends and side edges; and a pair of strap guiding channels extending through the strap clamping block in a longitudinal direction between said opposite side edges so as to present a first separator surface facing one of said opposite side edges and a second separator surface facing another of said opposite side edges, said first and second separator surfaces being non-adjustably fixed in position relative to the opposite flanks and respectfully diverging away from each other progressively along a direction that extends from the front end toward the rear end of said clamping block, the first and second separator surfaces have longitudinal lengths that are longer than longitudinal lengths of the transversely opposite side edges.

2. A strap clamping block according to claim 1, wherein a space defined between said opposite side edges in a vicinity of said rear end of said clamping block is reduced progressively along a direction that extends from said front end toward said rear end of said clamping block.

3. A strap clamping block according to claim 1, wherein a thickness of said clamping block as measured between said opposite flanks is smaller than a width of said clamping block as measured between said opposite side edges.

4. A strap clamping block according to claim 1, wherein each of said strap guiding channels is dimensioned, in a cross-section taken in a transverse direction of said clamping block, to have a length as measured in said transverse direction that is larger than a length as measured between said opposite flanks.

* * * * *

UNITED STATES PATENT AND TRADEMARK OFFICE
CERTIFICATE OF CORRECTION

PATENT NO. : 6,550,110 B1
DATED : April 22, 2003
INVENTOR(S) : Kawashima et al.

It is certified that error appears in the above-identified patent and that said Letters Patent is hereby corrected as shown below:

<u>Title page,</u>
Item [73], Assignee, should read -- Tabata Co., Ltd. --

Signed and Sealed this

Fourth Day of November, 2003

JAMES E. ROGAN
*Director of the United States Patent and Trademark Office*